United States Patent
Sigl et al.

(10) Patent No.: US 7,098,366 B2
(45) Date of Patent: Aug. 29, 2006

(54) SUPPORTED METAL OXIDES AS CATALYSTS FOR ALDOL CONDENSATIONS

(75) Inventors: Marcus Sigl, Mannheim (DE); Christian Miller, Ruppertsberg (DE); Walter Dobler, Schwetzingen (DE); Mathias Haake, Mannheim (DE)

(73) Assignee: BASF Aktiengesellschaft

( * ) Notice: Subject to any disclaimer, the term of this patent is extended or adjusted under 35 U.S.C. 154(b) by 55 days.

(21) Appl. No.: 10/497,597

(22) PCT Filed: Dec. 2, 2002

(86) PCT No.: PCT/EP02/13797

§ 371 (c)(1),
(2), (4) Date: Jun. 3, 2004

(87) PCT Pub. No.: WO03/047748

PCT Pub. Date: Jun. 12, 2003

(65) Prior Publication Data

US 2005/0070733 A1   Mar. 31, 2005

(30) Foreign Application Priority Data

Dec. 6, 2001 (DE) ............... 101 59 821
Jun. 12, 2002 (DE) ............... 102 26 120

(51) Int. Cl.
*C07C 45/72* (2006.01)
*B01J 23/00* (2006.01)
(52) U.S. Cl. .............. 568/390; 568/463; 502/302
(58) Field of Classification Search ........... 568/390, 568/463; 502/302
See application file for complete search history.

(56) References Cited

U.S. PATENT DOCUMENTS

| 3,578,702 A | 5/1971 | Snapp et al. ............ 260/486 |
| 4,270,006 A | 5/1981 | Heilen et al. ............ 568/396 |
| 4,521,630 A | 6/1985 | Wattimena et al. ...... 568/435 |

FOREIGN PATENT DOCUMENTS

| CA | 1 198 407 | 12/1985 |
| DE | 130457 | 3/1900 |
| EP | 013 385 | 7/1980 |
| EP | 085 996 | 8/1983 |
| NL | 1029844 | * 8/2000 |

OTHER PUBLICATIONS

Zhang et al. Aldol Addition of Acetone, Catalyzed by Solid Base Catalysts: Magnesium Oxide, Calcium Oxide, Strontium Oxide, Barium Oxide, Lanthanum (III) Oxide and Zirconium Oxide. Applied Catalysis, 1988, vol. 36, p. 189-197.*
ChemTech May 1997, XP008015170 Podrebarac et al. More uses for catalytic distillation p. 37-45.
Patent Abst. of Japan 62335014, date.
Derwent Abst. 83/742473/34, date.

* cited by examiner

*Primary Examiner*—Sikarl A. Witherspoon
(74) *Attorney, Agent, or Firm*—Novak Druce & Quigg, LLP; Jason D. Voight

(57) ABSTRACT

A supported catalyst is proposed comprising one or more metal oxides as active component on a catalyst support for carrying out an aldol condensation, with the catalyst support being γ-aluminum oxide, the active component comprising one or more oxides of the elements having atomic numbers 39 or from 57 to 71 and the concentration of the active component being in the range from 5 to 12% by weight, based on the weight of the catalyst support.

19 Claims, 4 Drawing Sheets

SUPPORTED METAL OXIDES AS CATALYSTS FOR ALDOL CONDENSATIONS

Figure 1:
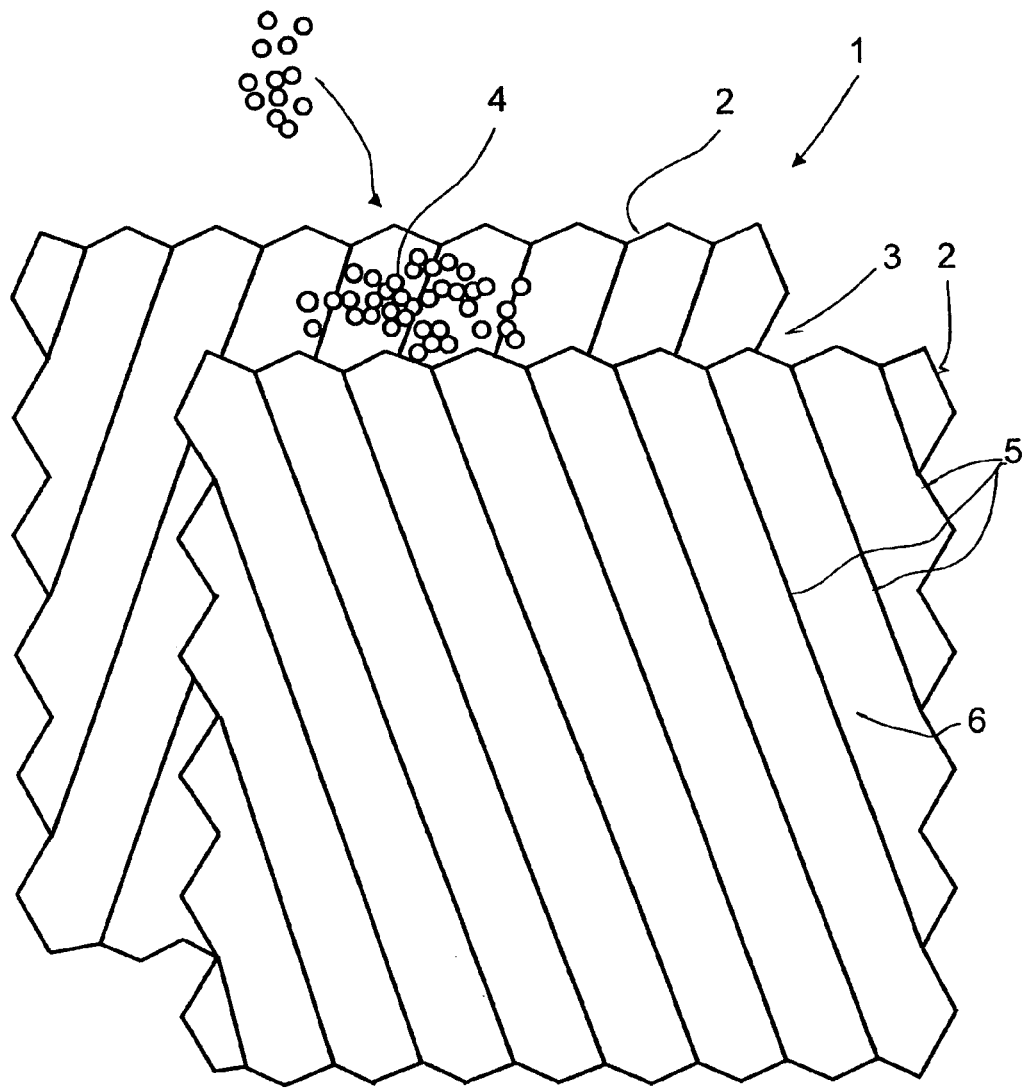

This application is the national stage application of PCT/EP02/13797, filed Dec. 2, 2002 and published as WO 03/047748 on Jun. 12, 2003.

The invention relates to a supported catalyst comprising one or more metal oxides as active component for carrying out an aldol condensation, a column for carrying out an aldol condensation by reactive distillation using a supported catalyst, and a process.

The term aldol condensation is used as is known to describe the generally base-catalyzed reaction of a carbonyl component with a methylene component. In this reaction the same compound can act simultaneously as carbonyl and methylene component. If different compounds are used as carbonyl component and methylene component in each case, it is frequently advantageous to use one of the components in excess, in particular in up to hundred-fold excess, compared with the other component.

In addition to homogeneous catalysis in the presence of aqueous alkali metal hydroxides or alkaline earth metal hydroxides, heterogeneous catalysis is known, for example by metal oxides of lanthanum or the lanthanides.

U.S. Pat. No. 3,578,702 describes the use of oxides of metals having atomic numbers from 57 to 71 as active component on a support of an inert material, for example aluminum oxide, kieselguhr, or preferably silica gel, the concentration of the active component being in the range from 0.5 to 10% by weight, based on the total weight of the supported catalyst.

It is an object of the present invention, in contrast, to provide supported catalysts for carrying out an aldol condensation which are distinguished in comparison with known supported catalysts by an increased catalyst activity and an improved space-time yield.

We have found that this object is achieved by a supported catalyst comprising one or more metal oxides as active component for carrying out an aldol condensation, with the catalyst support being γ-aluminum oxide, the active component comprising one or more oxides of the elements having atomic numbers 39 or from 57 to 71 and the concentration of the active component being in the range from 5 to 12% by weight, based on the total weight of supported catalyst.

As a result of extensive screening studies, it has surprisingly been found that a significant improvement in catalyst activity is achieved, with the above-defined conditions being maintained.

The inventive supported catalysts are preferably suitable for carrying out the aldol condensation of citral and acetone to give pseudoionone. Pseudoionone is an important intermediate for vitamin and fragrance production. Advantageously, citral is used in a molar ratio to acetone of 1–2:50. Reaction temperatures from 30 to 100° C. and pressures from 1 to 10 bar absolute are particularly advantageous.

It has been found that suitable selection of the catalyst support critically affects catalyst activity. Using γ-aluminum oxide as catalyst support, markedly improved space-time yields were obtained.

In a preferred embodiment, the geometry of the catalyst support is determined in such a manner that the ratio of the outer surface area to the volume is in the range from 0.5 to 10 mm$^{-1}$, preferably in the range from 1 to 5 mm$^{-1}$, in particular that the catalyst support is present in the form of solid or hollow cylinders, spheres, honeycombs, trilobes or toothed wheels.

A further condition which is critical for the activity of the inventive supported catalyst is maintaining the concentration of the active component which, according to the invention, must lie in the range from 5 to 12% by weight, based on the total weight of the supported catalyst. It has been found that when the concentration is maintained in the abovementioned range, good space-time yields are obtained and that concentrations outside said limiting values lead to a decrease in space-time yield.

Particularly advantageous are concentrations of the active component in the range from 7.5 to 10% by weight, based on the total weight of the supported catalyst.

The inventive supported catalysts can be used in principle in any reactor suitable for heterogeneously catalyzed reactions. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column. The reaction can be performed at differing temperatures and pressures, the optimum being defined by the starting materials used. Generally, the reaction temperatures are from 20 to 200° C. and the pressures from 0.1 to 100 bar absolute.

A particular advantage of the inventive supported catalysts is that simple regeneration is possible by calcining, or by washing with alkaline solutions. It has been found that in the event of a decrease in catalyst activity, which is observable in a reduction in space-time yield, it is possible to regenerate the catalyst and to restore the original activity. The regeneration can be carried out by treating with aqueous alkaline solutions, in particular alkali metal hydroxide, alkaline earth metal hydroxide or ammonium hydroxide solutions, or by calcining in the presence of oxygen at temperatures from 150 to 700° C. In addition, it is also possible to increase the activity of the fresh catalyst by a base treatment before use in the aldol condensation. Regeneration and also pretreatment indicate a base-catalyzed mechanism for the aldol condensation.

The invention also relates to a column for carrying out an aldol condensation by reactive distillation in the presence of a heterogeneous particulate catalyst having a structured packing or random packings which form interstices in the column interior, the quotient of the hydraulic diameter for the gas flow through the structured packing or the random packings and the equivalent diameter of the catalyst particles being in the range from 2 to 20, preferably in the range from 5 to 10, in such a manner that the catalyst particles are introduced into the interstices, distributed and discharged loose under the action of gravity, and the catalyst particles used being supported catalysts as described above.

The hydraulic diameter is defined as is known as the ratio between four times the area through which flow passes and the circumference thereof. Actual calculation of the same for a structured packing having linear folds is explained in the description of the figures, in connection with FIG. 2.

The hydraulic diameter of random packings is determined via the porosity of the bed ψ, that is to say void volume of the bed/total volume and the equivalent diameter of the random packings, $$d_{hydraulic} = \frac{d_p \times \psi}{1 - \psi},$$

where $d_{hydraulic}$=hydraulic diameter, $d_p$=diameter of the random packings and ψ=porosity. The equivalent diameter of the random packings is defined by the ratio between six times the volume and the surface area of the random packing (see VDI Wärmeatlas [VDI Thermal Handbook], 5th edition, 1988, Lk 1).

The equivalent diameter of particles, in the present case catalyst particles, is defined by the ratio between six times the volume and the surface area of the particle (see in this context VDI Wärmeatlas [VDI Thermal Handbook], 5th edition, 1988, Lk 1).

Maintaining a quotient of the hydraulic diameter for the gas flow through the structured packing or the random packings and the equivalent diameter of the catalyst particles within the above-defined range ensures according to the invention that the catalyst particles are introduced into the interstices of the structured packing or the random packings, distributed and discharged loose under the action of gravity.

With respect to the structured packings or random packings which can be used, there are in principle no restrictions: column internals can be used which are regularly used in distillation technology in order to increase the interfacial area between the phases moving in countercurrent through the column, the gaseous phase and the liquid phase. The structured packings or random packings in the column interior form interstices which must in principle be connected to one another in order to ensure the counterflow of gaseous and liquid phases which is required for the separation action by distillation.

The inventors have thus found that it is possible in principle to introduce catalyst particles into the mutually connected interstices which make up the structured packing or the random packings in the column interior, to distribute them and discharge again the spent catalyst particles loose under the action of gravity.

It must be ensured here that sufficient free interstices are present for the gas flow which results from the distillation, so that there is no backing-up of the liquid stream flowing in countercurrent to the gas stream. This is ensured according to the invention by the quotient of the hydraulic diameter for the gas stream through the structured packing or through the random packings and the equivalent diameter of the catalyst particles being selected very small, that is to say having values within the above-defined ranges.

The invention is not limited with respect to the shape and size of the usable catalyst particles; however, to improve the space-time yield high specific surface areas and thus small catalyst particles are preferred. In beds of catalyst particles, as is known, the pressure drop increases with increasingly smaller catalyst particles and limits, in the case of a reactive distillation, the liquid and vapor throughputs to uneconomically small values. Because of the generally highly pronounced channeling of liquid in catalyst beds, for large column diameters which are required in industrial-scale plants only low separation efficiencies by distillation are achieved. These disadvantages have prevented hitherto the use, which is desirable per se, of catalyst beds as separation internals in reactive distillations. In contrast, according to the invention, precisely small catalyst particles, which are also preferred with respect to catalytic activity, are particularly suitable for combined use with a structured packing or with random packings, since they are simpler to introduce the smaller are their dimensions compared with the dimensions of the interstices of the structured packing or random packings.

Suitable dimensions of the catalyst particles are, for example for solid cylindrical catalyst particles, from about 1×4 mm to about 4×40 mm.

Preferably, as column internals, structured packings are used, that is to say packings made up systematically in a regular geometry having defined passage regions for counterflow phases. Structured packings are generally made up of metal sheets, expanded metal layers or wire mesh layers essentially arranged in parallel to one another. Compared with other column internals, they are distinguished by a higher load capacity, improved separation efficiency and a lower specific pressure drop. Structured packings are generally made up of corrugated metal sheets, expanded metal layers or mesh layers essentially arranged in parallel to one another, having usually linear corrugations which subdivide the sheet metal packing, the expanded metal layer or mesh layer into corrugated surfaces and in which case the angle of inclination of the corrugated surface to the vertical is usually from 30 to 45°. For the present invention, structured packings having an angle of inclination of the corrugated surface to the vertical in the range from 10 to 45°, preferably 30°, can be used. By arranging successive structured packing sheets at the same angle of inclination to the vertical, but with reversed sign, the known cross-channel structures are produced, as are exhibited, for example, by packings of the types Mellapak, CY or BX from Sulzer AG, CH-8404 Winterthur or types A3, BSH, B1 or M from Montz GmbH, D-40723 Hilden.

For use in reactive distillation, preferably, special embodiments of structured packings are used which permit an increased gas flow.

In a particularly preferred embodiment, one or more structured sheet metal packings of high specific surface area are arranged in alternation with one or more structured sheet metal packings of low specific surface area. As a result interstices each having different hydraulic diameter are formed. Particularly preferably, the specific surface areas of the structured sheet metal packings are chosen in such a manner that firstly interstices are formed for which the quotient of hydraulic diameter and equivalent diameter of the catalyst particles is less than 1, and secondly interstices for which the quotient of hydraulic diameter and equivalent diameter of the catalyst particles is greater than 2, in particular in the above-defined range from 2 to 20, in particular from 5 to 10. No catalyst particles are charged into the first-mentioned interstices having a ratio of hydraulic diameter and equivalent diameter of catalyst particles less than 1; the same are according to the invention only charged into the interstices in which said quotient is greater than 2. This particular embodiment ensures an increased gas flow with low pressure drops.

Preferably, the starting material for inventive structured packings is usually additionally supplied with openings, for example with circular holes of diameter from about 4 to 6 mm, in order to increase the flooding point of the structured packing and to enable higher column loading. Flooding point of a structured packing is the volume of gas or liquid per unit time and per unit area of cross section in which the trickling liquid is backed up or entrained by the gas stream in and above the packing to the point of complete flooding. Exceeding this loading causes a rapid decrease in separation efficiency and a sharp increase in pressure drop.

Instead of structured packings, equally, random packings can be used, in which case, in principle, there are no limits with respect to the shape of the same. Thus, for example, all shapes of random packings known in distillation technology can be used, such as Raschig rings, Pall rings or saddles.

Structured packings or random packings which have horizontal surface portions are advantageous. The horizontal surface portions receive some of the weight of the catalyst particles and divert it to the column wall. As a result the mechanical loading of the catalyst is decreased.

Preference is given to structured packings which are formed from structured sheet metal packings for vertical installation into the column having linear corrugations which subdivide the stuctured sheet metal packing into corrugated surfaces, the angle of inclination of the corrugated surfaces to the horizontal being in the range from 90 to 45°, preferably 60°.

The specific surface area of structured packings for distillation is from about 250 to 750 m$^2$/m$^3$. For columns for carrying out heterogeneously catalyzed reactive distillations, structured packings having lower specific surface areas, in the range from about 50 to 250 m$^2$/m$^3$ are preferably used.

In the case of structured packings for distillation, wall thicknesses of the metal sheets of typically from 0.07 to 0.1 mm suffice. In contrast, in the case of heterogeneously catalyzed reactive distillations, depending on catalyst weight and mechanical stability of the catalyst grains, wall thicknesses of the metal sheets in the range from 0.1 to 5 mm, preferably from 0.15 to 0.3 mm, are used.

Preferably, structured packings or random packings are used which have a reduced resistance to flow at their surface, this reduced resistance to flow being achieved in particular by perforations and/or roughness of the material of the structured packing or of the random packings or by constructing the structured packing as expanded metal. The perforations here are preferably dimensioned with respect to their number and dimensions in such a manner that at least a proportion of 20%, preferably a proportion of from 40 to 80%, of the liquid reaction mixture passes through these perforations and flows onto the catalyst particles lying beneath them.

In a preferred embodiment, the structured packing material consists of expanded metal, the structured packing material being constructed in such a manner that the liquid flowing off on the packing material as film can flow off as completely as possible through the packing material downward, dripping being reinforced by outlet edges.

Preferably, the perforations are provided in the vicinity of the lower corrugated edges of the structured sheet metal packings arranged vertically in the column, as described in DE-A 100 31 119. As a result, the fluid is preferably passed onto the upper side of the inclined corrugated surfaces and the liquid loading on the critical lower side is decreased. For this, structured packings made of structured sheet metal packings are used for vertical installation into the column having linear corrugations which subdivide the structured sheet metal packings into corrugated surfaces and which have a width a measured from corrugated edge to corrugated edge and perforations, and in which a proportion X of at least 60% of the perforations has a distance b of at most 0.4 a to the lower corrugated edge of each corrugated surface. Preferably, the proportion of the area taken up by the perforations of a corrugated surface is from 5 to 40%, in particular from 10 to 20%, of this corrugated surface.

In a further preferred embodiment, the structured packing is formed from rippled or corrugated layers, and between two rippled or corrugated layers in each case one flat intermediate layer is disposed, with the flat intermediate layers not extending to the edge of the structured packing or having, in the edge zone of the structured packing, an increased gas permeability, in particular holes, in accordance with DE-A 196 01 558.

It is also possible to provide, instead of flat intermediate layers, less intensively rippled or corrugated layers.

The term edge zone of the structured packing is applied to a concentric volume element which extends from an outer cylinder surface to an inner cylinder surface (the structured packings typically have a cylindrical shape), with the outer cylinder surface being defined by the outer ends of the rippled or corrugated layers and the inner cylinder surface being defined by the outer ends of the flat layers. The horizontal line connecting the inner cylinder surface to the outer cylinder surface and which is oriented in parallel to the packing layers and passes through the column axis intersects from one to twenty, preferably from three to ten, channels formed by each of the layers disposed next to one another. In the case of flat layers which do not extend into the edge zone, thus up to twenty channels are cleared next to one another in the edge zone. Second layers extending into the edge zone are preferably gas-permeable on from 20 to 90% of their surface, particularly preferably from 40 to 60% of their surface, that is to say, for example, provided with holes.

At the points at which the channels formed by the metal sheets contact the column wall, damming of the ascending gas stream occurs, because the channels are closed by the column wall. This leads to a markedly poorer separation efficiency of the structured packing. By opening the structured packing channels in the wall zone, this cause of a decreased separation efficiency can be eliminated in a simple and effective manner. The gas can in this case transfer from the channels ending at the column wall into other channels which lead it in the opposite direction.

The invention also relates to a process for preparing pseudoionone by aldolizing citral and acetone by reactive distillation in a column, as described above. Preferably, the column is operated with respect to its gas and liquid loading in such a manner that a maximum of from 50 to 95%, preferably from 70 to 80%, of the flooding limit loading is reached.

The invention will now be described in more detail below with reference to a drawing and examples.

In the drawings

Figure 2:
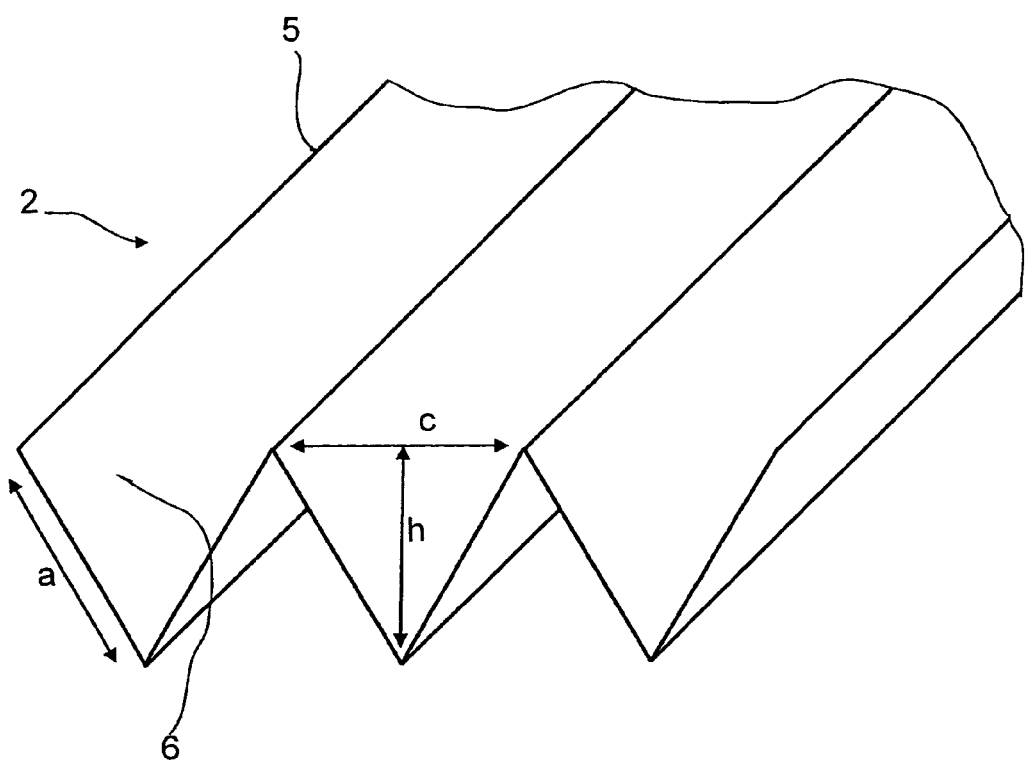
Figure 3:
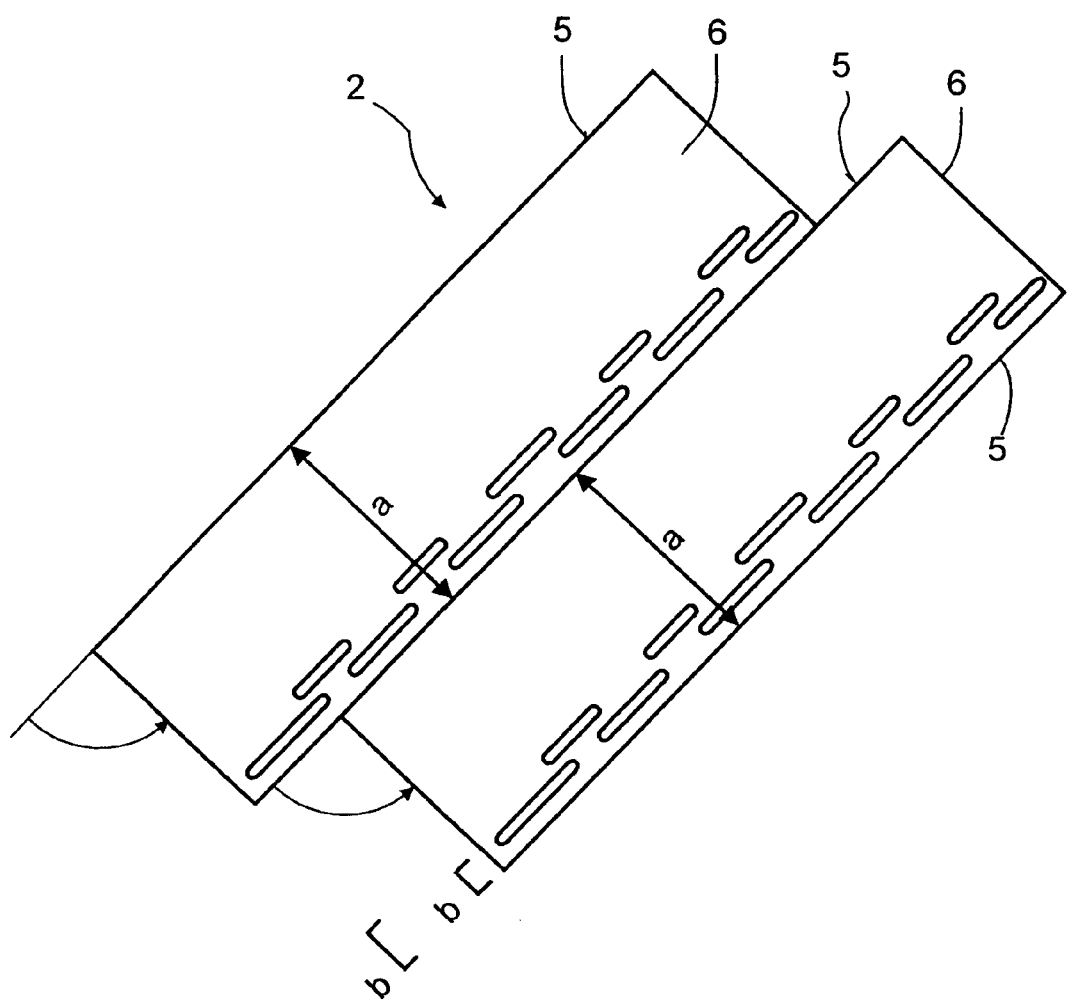
Figure 4:
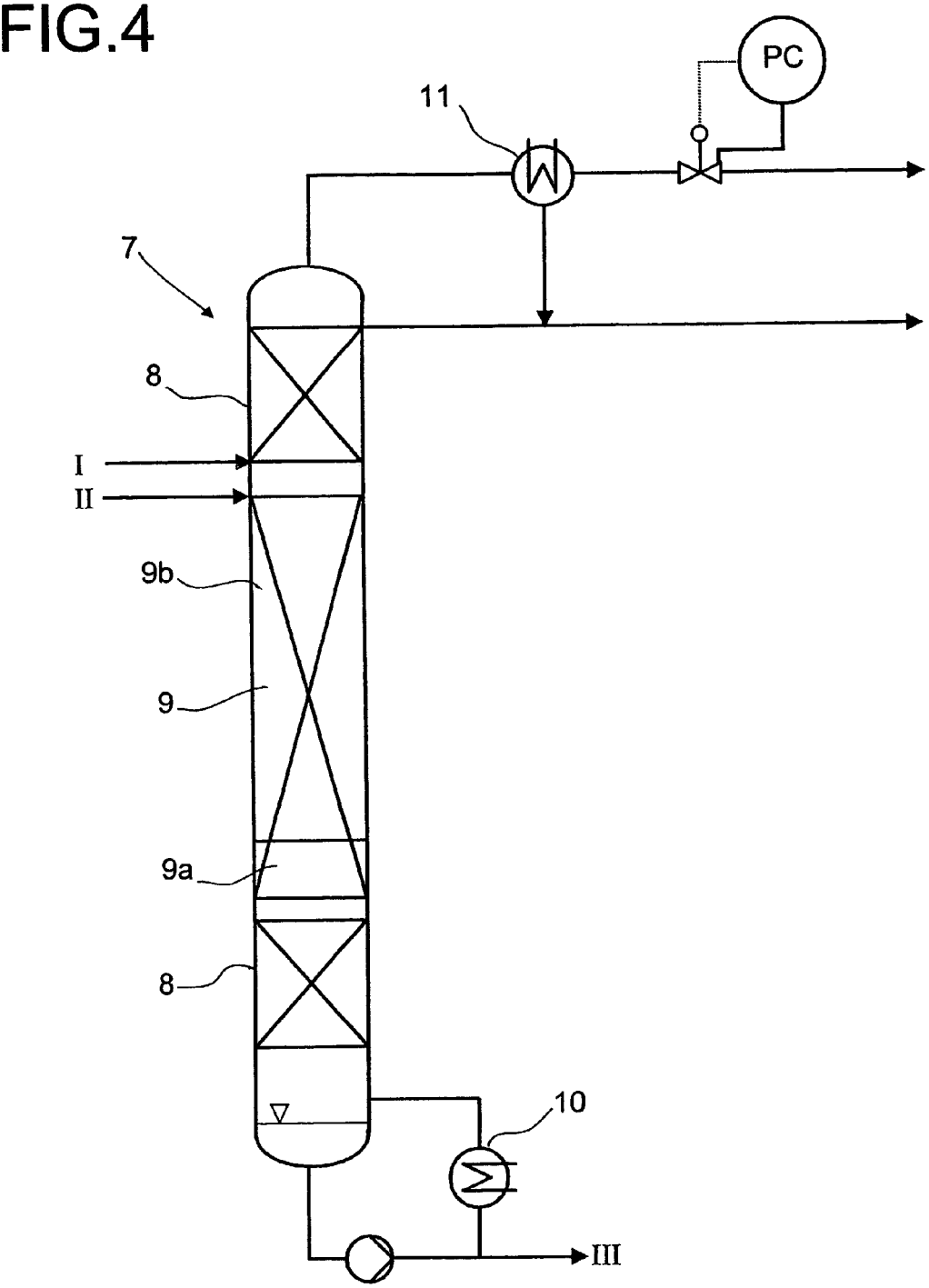

FIG. 1 shows a diagrammatic representation of an embodiment of an inventive structured packing, FIG. 2 shows a diagrammatic representation of a structured sheet metal packing having linear corrugations and FIG. 3 shows a diagrammatic representation of a structured sheet metal packing having perforations and FIG. 4 shows a diagrammatic representation of an embodiment of an inventive column.

The diagrammatic representation in FIG. 1 shows a structured packing 1 having structured sheet metal packings 2 which have linear corrugations 5 with formation of corrugated surfaces 6, with in each case an interstice 3 being formed between two sequential structured sheet metal packings 2. According to the invention catalyst particles 4 are charged into the same interstices.

FIG. 2 shows diagrammatically a structured sheet metal packing 2 having linear corrugations 5 and corrugated surfaces 6, a is the width of a corrugated surface 6 measured from corrugated edge 5 to corrugated edge 5, c represents the distance between two adjacent corrugated edges 5 and h represents the height of a corrugation.

FIG. 3 shows diagrammatically a particular embodiment of a structured sheet metal packing 2 having corrugated edges 5, corrugated surfaces 6 and a width a of the corrugated surfaces 6 having perforations which have a distance b from the lower corrugated edge 5 of each corrugated surface 6.

The reactive distillation column 7 shown diagrammatically in FIG. 4 has two pure separation zones 8, respectively in the upper and lower region of the reactive distillation column 7, which are fitted with structured fabric packings. In the middle column region is arranged a reaction zone 9 which has a lower region 9a containing a structured packing without introduced catalyst particles and an upper region 9b containing an inventive structured packing having introduced catalyst particles. The reactive distillation column 7 is fitted with a bottoms reboiler 10 and a condenser 11 at the column top. The starting materials are applied in the upper region of the column as streams I and II, the reaction mixture is taken off as bottoms stream III and an overhead stream IV is taken off at the column top. A pressure controller PC is disposed at the column top.

EXAMPLES

Example 1

Loose Packing Experiments

A column section having a diameter of 0.3 m was fitted with two structured distillation packings arranged offset by 90° of type B1 from Montz, the height of each structured packing being 23 cm. Catalyst particles were introduced by loose packing into the structured distillation packings. The fill volume and the ease of handling during introduction and removal of the catalyst particles were determined. The catalyst particles used were solid cylinders of $\gamma$-$Al_2O_3$ coated with 5% praseodymium oxide. The solid $\gamma$-$Al_2O_3$ cylinders of a diameter of 1.5 mm and a height of from 1 to 4 mm have an equivalent particle diameter of 2 mm.

1A) Loose packing experiments using solid $\gamma$-$Al_2O_3$ cylinders, diameter 1.5 mm. Structured packings of type B1 from Montz each having different specific surface areas and different angles of inclination of the corrugated surfaces to the horizontal were used.

1A$_1$) A structured sheet metal packing of type B1-125.80 having a specific surface area of 125 $m^2/m^3$ and an angle to the horizontal of 80° was used. 90% of the superficial volume was packed with the above-mentioned catalyst particles. The structured packing had a hydraulic diameter of 19 mm. The catalyst was able to be introduced very readily and in the dry state also trickled out again completely. The ratio of the equivalent diameter of the catalyst particles to the hydraulic diameter of the structured packing was 9.

1A$_2$) A structured packing of type B1-250.80 having a specific surface area of 250 $m^2/m^3$ and an angle to the horizontal of 80° was packed with the abovementioned catalyst particles. In this case 80% of the superficial volume was able to be packed with catalyst particles. The structured packing had a hydraulic diameter of 9.4 mm. The catalyst was able to be introduced very readily and in the dry state also trickled out again completely. The ratio of equivalent diameter of the catalyst particles to the hydraulic diameter of the structured packing was 4.7.

1A$_3$) A structured packing of type B1-250.60 was used, that is to say having a specific surface area of 250 $m^2/m^3$ and an angle to the horizontal of 60°. 80% of the superficial volume of the same was able to be packed with the abovementioned catalyst particles. The structured packing had a hydraulic diameter of 9.4 mm. The catalyst was able to be introduced very readily and in the dry state also trickled out again completely. The ratio of the equivalent diameter of the catalyst particles to the hydraulic diameter of the structured packing was 4.7.

In contrast, in the case of commercially conventional catalyst packings in which the catalyst is introduced in pockets, for example of the type Katapak from Sulzer or Multipak from Montz, only from 20 to 30% of the superficial volume, in exceptional cases a maximum of 50% of the superficial volume, could be packed with catalyst.

Example 2

Pressure Drop Measurements

In a column section of diameter 0.1 m, pressure drop measurements were made using the test mixture nitrogen/isopropanol. For this, the catalyst bed was introduced into the column section and irrigated (one drip position) with a defined amount of isopropanol. In countercurrent to this, a defined amount of nitrogen was passed through the structured packing/bed from bottom to top. In the experiments the specific pressure drop per unit height of structured packing or bed was measured and the flooding point was determined. The catalyst particles used were solid $\gamma$-$Al_2O_3$ cylinders coated with 5% praseodymium oxide. The solid cylinders (d=1.5 mm, h=1–4 mm) had an equivalent particle diameter of 2 mm. The specific pressure drop and the flooding point of a bed introduced into a structured packing were then determined.

Example 2

Comparative Example

At a bed height of 45 cm, at an F factor of 0.038 $Pa^{0.5}$ (corresponding to a gas flow rate of 1 000 l/h) and a liquid loading of 0.178 $m^3/m^2h$ (corresponding to a liquid flow rate of 1.4 l/h), a specific pressure drop of 3.33 mbar/m was measured. The structured packing began to flood, at a constant liquid loading of 0.178 $m^3/m^2h$, from an F factor of 0.0575 $Pa^{0.5}$ (corresponding to a gas flow rate of 1 500 l/h).

Example 2

According to the Invention

Bed introduced into two layers, offset by 90°, of a structured packing of type BS-250.60 from Montz.

At a bed height of 46 cm, at an F factor of 0.038 $Pa^{0.5}$ (corresponding to a gas flow rate of 1 000 l/h) and a liquid loading of 0.178 $m^3/m^2h$ (corresponding to a liquid flow rate of 1.4 l/h), a specific pressure drop of 1.09 mbar/m was measured. The structured packing began to flood, at a constant liquid loading of 0.178 $m^3/m^2h$, from an F factor of 0.114 $Pa^{0.5}$ (corresponding to a gas flow rate of 3 000 l/h). The maximum gas loading could thus be increased by a factor of 2 compared with the bed which was not introduced into a structured packing.

Below, with reference to FIG. 2, the calculation of the hydraulic diameter for a structured packing having linear corrugations is described:

The structured sheet metal packing 2 shown by way of example in FIG. 2 has linear corrugations 5 arranged in parallel to one another, which corrugations subdivide the structured sheet metal packing 2 into corrugated surfaces 6. The width of a corrugated surface 6, measured from corrugated edge 5 to corrugated edge 5, is designated a, the distance between two sequential corrugated edges 5 is designated c and the height of the corrugation is designated h. The hydraulic diameter of the gas flow for a structured packing made up of such structured sheet metal packings is then calculated using the equation $$d_{hydraulic,gas} = \frac{2c \cdot h}{c + 2a}$$

Example 3

Catalyst Screening 3.1 Catalyst Preparation

The supported catalysts to be tested were prepared in the standard way by impregnating pore volume. For this the support was impregnated with the active component in the form of a metal salt solution, dried in a drying cabinet at 120° C. and then calcined under air. Unless otherwise stated, the calcination was performed for 2 h at 450° C. at a heating rate of 3.5° C./min.

To prepare catalysts having praseodymium oxide as active component, a praseodymium nitrate stock solution of 1 170 g of praseodymium oxide, 2 276 g of 65% strength nitric acid and 1 557 g of water was used. This solution contained 18.1% by weight of praseodymium oxide and was then diluted with deionized water, depending on the liquid absorption of the support.

3.2 Catalyst Screening

The purpose of catalyst screening was to find catalysts having a high space-time yield and thus high catalyst activity.

The catalyst was screened in an apparatus consisting of a reservoir vessel, pump and heated metal tubular reactor. From the reservoir vessel was passed a mixture of 79% by weight of acetone and 21% by weight of citral at a mass flow rate of 200 g/h using a pump from bottom to top through the trace-heated tubular reactor packed with 50 g of catalyst. The reaction was carried out at 90° C. and 2.5 bar$_{absolute}$. Sampling was performed after 2, 4 and 6 h, and the values thus obtained were averaged.

3.3 Analysis

Samples were analyzed by gas chromatography (GC). The concentrations of the individual components were determined using an internal standard (N-methyl-pyrrolidone, NMP). The analytical method data may be taken from the table below:

| GC separation method for analyzing the reaction of citral and actone to form pseudoionone | |
|---|---|
| GC system: | HP5890 and 6890 |
| Separation column: | HP5-025 film 30 m × 0.32 mm |
| Detector: | FID |
| Temperature program: | 60° C.     1 min |
| | 60 → 150° C.  10° C./min |
| | 150 → 200° C.  20° C./min |
| | 200° C.    10 min |
| | 200 → 240° C.  10° C./min |
| | 240° C.    5 min |
| Internal standard: | 0.1 g NMP to 0.7 g of sample |

| GC separation method for analyzing the reaction of citral and actone to form pseudoionone | |
|---|---|
| Components monitored | |
| Name | Retention times (min) |
| Acetone | 2.9 |
| Mesityl oxide (2-methyl-2-penten-4-one) | 4.5 |
| Diacetone alcohol (4-hydroxy-4-methyl-2-pentanone) | 5.3 |
| Citral | 11.9 |
| Pseudoionone | 15.9 |

3.4 Variation in Catalyst Support Composition

All support materials tested for the catalyst support were each coated with 5% praseodymium oxide as active component. By varying the catalyst support composition, the results listed in the table below were obtained:

The abbreviation BET in the table heading indicates, as is known, the catalyst surface area determined by the method of Stephen Brunauer, Paul Emmett and Edward Teller, as specified in DIN 66131. STY denotes the space-time yield in g PSI/g Cat/h, that is to say in grams of pseudoionone per gram of catalyst and hour.

TABLE 1

| Example | Support material | Shaped body/diameter [mm] | BET [m$^2$/g] | STY [g PSI/g Cat/h] |
|---|---|---|---|---|
| According to the invention | γ-Al$_2$O$_3$ | Rod/4 | | 0.49 |
| Comparison | δ/υ-Al$_2$O$_3$ | Sphere/2 | | 0.01 |
| Comparison | SiO$_2$ | Rod/4 | 173 | 0 |
| Comparison | SiO$_2$ | Rod/4 | 92 | 0.02 |
| Comparison | TiO$_2$ | Rod/1.5 | 100 | 0.27 |
| Comparison | Bleached earth | Rod/1.5 | | 0.01 |

The results in the table show that among the tested support materials, γ-aluminum oxide had by far the best space-time yield.

3.5 Variation in Catalyst Support Geometry

The abbreviations in the table headings have the same meanings as listed above under number 3.4. The space-time yields were also determined under the same conditions as under 3.4, that is to say with a 5% praseodymium oxide coating on the catalyst support. The experimental results are summarized in the table below:

TABLE 2

| Example | Support material | Shaped body/diameter [mm] | BET [m$^2$/g] | STY [g PSI/g Cat/h] |
|---|---|---|---|---|
| Comparison | γ-Al$_2$O$_3$ | Rod/4 | 215 | 0.43 |
| Comparison | γ-Al$_2$O$_3$ | Rod/3 | 178 | 0.45 |
| According to the invention | γ-Al$_2$O$_3$ | Trilobe/3 | 221 | 0.53 |
| According to the invention | γ-Al$_2$O$_3$ | Rod/1.5 | 200 | 0.53 |

TABLE 2-continued

| Example | Support material | Shaped body/diameter [mm] | BET [m²/g] | STY [g PSI/g Cat/h] |
|---|---|---|---|---|
| According to the invention | γ-Al$_2$O$_3$ | Trilobe/1.4 | | 0.62 |
| According to the invention | γ-Al$_2$O$_3$ | Toothed wheel/5.9 | | 0.60 |
| According to the invention | γ-Al$_2$O$_3$ | Honeycomb/5.7 | | 0.50 |
| According to the invention | γ-Al$_2$O$_3$ | Rod/1.2 | 243 | 0.56 |
| According to the invention | γ-Al$_2$O$_3$ | Sphere/1.8 | 216 | 0.62 |

The results in the table show that the use of catalyst supports having a high ratio of external surface area to volume leads to catalysts having good space-time yields. Thus the catalyst supports indicated as comparison having geometries of 4 mm and 3 mm rods exhibit space-time yields <0.5 g of pseudoionone/g of catalyst/h (comparative experiments in the first two rows of the table).

In contrast, the inventive examples in rows 3 to 9 of the table show that thinner rods, smaller spheres and special geometries (trilobes, toothed wheels and honeycombs), that is to say catalyst support geometries having greater external surface area in relation to volume, have improved space-time yields in the range from 0.5 to 0.6 g of pseudoionone/g of catalyst/h.

3.6 Variation in the Praseodymium Oxide Content

γ-Aluminum oxide rods having a diameter of 1.5 mm were coated in the manner described above under 3.1 with differing contents of praseodymium oxide. The experimental results are summarized in table 3 below.

TABLE 3

| Example | Praseodymium oxide content | STY [g PSI/g Cat/h] |
|---|---|---|
| Comparison | none | 0.24 |
| Comparison | 2.5% | 0.49 |
| According to the invention | 5% | 0.56 |
| According to the invention | 7.5% | 0.68 |
| According to the invention | 10% | 0.70 |
| Comparison | 33% | 0.48 |

The results of the table show that the space-time yield passes through a maximum at a praseodymium oxide coating between 7.5 and 10% by weight. Higher coatings lead to a decrease again in space-time yield. This decrease in activity at higher coatings is also exhibited visually: the originally weak green color of the supported catalyst changed to brown. Agglomeration of the praseodymium oxide particles could be responsible for this.

3.7 Variation in Composition of the Active Component

The support used was γ-aluminum oxide rods having a diameter of 1.5 mm coated with active components in the manner described above under 3.1. In this case, in all cases the starting material used was the nitrate solution of the corresponding metals, except for zinc which was used as zinc acetate solution. In all cases a coating with 5% of the respective active component was carried out.

The abbreviation LnO-Mix indicates a commercial rare earth metal mixture from Rhone-Poulenc having the composition: 13.87% CeO$_2$/7.69% La$_2$O$_3$/1.65% PrO$_x$/5.69% Nd$_2$O$_3$.

The results are listed in table 4 below.

TABLE 4

| Example | Active component | STY [g PSI/g Cat/h] |
|---|---|---|
| According to the invention | Y$_2$O$_3$ | 0.75 |
| According to the invention | La$_2$O$_3$ | 0.54 |
| According to the invention | CeO$_x$ | 0.54 |
| According to the invention | PrO$_x$ | 0.56 |
| According to the invention | Nd$_2$O$_3$ | 0.62 |
| According to the invention | LnO-Mix | 0.60 |
| Comparison | BaO | 0.33 |
| Comparison | Al$_2$O$_3$ | 0.26 |
| Comparison | Bi$_2$O$_3$ | 0.29 |
| Comparison | Fe$_2$O$_3$ | 0.32 |
| Comparison | ZnO | 0.43 |

Example 4

Preparation of Pseudoionone by Aldolization of Citral and Acetone

The experimental setup corresponded to the diagrammatic representation in FIG. 4. The reactive distillation column 7 was packed in each of the separation zones 8 with one segment of a structured fabric packing of type A3-500 from Montz, having a total height in each case of 23 cm. The reaction zone 9 was fitted in the lower region of the same with one layer of Montz-Pak type B1-1000 in a special element height of 30 mm. This layer served as catalyst barrier so that the catalyst particles could not trickle into the lower separation zone. On this layer were installed three layers of Montz-Pak of type B 1-250.60 having an element height of 212 mm, into which the catalyst was introduced by loose packing. 3 121 g of catalyst were packed in this case at a bulk density of 700 kg/m$^3$. The catalyst used was solid cylinders of 5% praseodymium on γ-Al$_2$O$_3$ having a particle diameter of 1.5 mm and a height of from 1 to 4 mm, which had been prepared by impregnating γ-Al$_2$O$_3$ with an aqueous solution of praseodymium nitrate and subsequent calcination. The column was fitted at regular intervals with thermocouples and with sampling points, so that the temperature profile and concentration profile in the column could be determined.

The reactants citral and acetone (streams I and II, respectively, in FIG. 4) were metered into the reactive distillation column from reservoir vessels standing on balances, with mass flow controlled by a pump.

The bottoms reboiler 10 which was heated to 124° C. using a thermostat had a holdup from 50 to 150 ml during operation, depending on residence time. The bottoms stream III was transported under level control by a pump from the bottoms reboiler 10 into a vessel standing on a balance.

The overhead stream from the reactive distillation column was condensed in a condenser 11 which was operated using a cryostat. A portion of the condensate passed via a reflux divider, as stream IV, into a reservoir vessel standing on a balance, while the other portion was applied to the column as reflux. The apparatus was equipped with a pressure controller PC and designed for a system pressure of 20 bar. All influent and effluent streams were continuously detected and recorded during the entire experiment using a process control system PCS. The apparatus was operated continuously in 24 hour operation.

A stream I of 220.0 g/h, equivalent to 1.4 mol/h of citral having a purity of 97%, and a stream II of 840.0 g/h, equivalent to 14.32 mol/h of acetone preheated to 80° C. having a purity of 99% were continuously applied to the above-described reactive distillation column 7.

Experimental Procedure

The catalyst used in the reaction zone 9 was solid cylinders (d=1.5 mm, h=1–4 mm) of 5% Pr on γ-$Al_2O_3$. A system pressure of 3 bar and a reflux ratio of 3 kg/kg was set. The bottom temperature was 92.50. The bottoms stream III of the column obtained was 735.6 g/h of crude product containing 62.14% by weight of acetone, 0.71% by weight of water, 0.45% by weight of mesityl oxide, 0.95% by weight of diacetone alcohol, 9.14% by weight of citral, 24.43% by weight of pseudoionone and 2.18% by weight of high boilers. At the top of the column, 323.2 g/h of distillate (stream IV) were taken off, consisting of 95.8% by weight of acetone and 4.2% by weight of water.

Pseudoionone was obtained with a selectivity of 97.3% based on citral and 84.4% based on acetone. The yield was 66.7% based on citral.

At F factors of 0.12 $Pa^{0.5}$ and liquid loadings of 0.3 $m^3/m^2h$, a differential pressure of approximately 1 mbar was measured over the column.

When an uncontrolled catalyst bed without structured packing was used, in comparison twice the pressure drop was measured.

The differential pressure is a measure of the loading (gas and liquid) of the column. Depending on material properties and the type of internals used, the differential pressure increases with increasing loading until flooding occurs. In the flooding state, the catalyst is swirled up and high catalyst abrasion can occur. This state must therefore be avoided.

When an inventive structured packing is used, therefore, a higher throughput can be achieved for the same column diameter.

We claim:

1. A method of using supported catalyst consisting of one or more oxides of the elements having atomic numbers 39 or from 57 to 71 as active component on γ-aluminum oxide as a catalyst support, the concentration of the active component being in the range from 5 to 12% by weight, based on the weight of the γ-aluminum oxide catalyst support, for carrying out a heterogeneously catalyzed aldol condensation.

2. The method as claimed in claim 1, wherein the concentration of the active component is in the range from 7.5 to 10% by weight, based on the weight of the catalyst support.

3. The method as claimed in claim 1, wherein the geometry of the catalyst support is determined in such a manner that the ratio of the external surface area to the volume is in the range from 0.5 to 10 $mm^{-1}$.

4. The method as claimed in claim 1, wherein the active component is yttrium oxide.

5. The method as claimed in claim 1, wherein the active component is praseodymium oxide.

6. A method of using a column for carrying out an aldol condensation by reactive distillation in the presence of a heterogeneous particulate catalyst having a structured packing or random packings which form interstices in the column interior, in which the quotient of the hydraulic diameter for the gas flow through the structured packing or the random packings and the equivalent diameter of the catalyst particles is in the range from 2 to 20 in such a manner that the catalyst particles are introduced into the interstices, distributed and discharged loose under the action of gravity, and the catalyst particles are formed from a supported catalyst according to the definition in claim 1.

7. The method as claimed in claim 6, wherein the structured packing is preferably a cross-channel packing.

8. The method as claimed in claim 6, wherein the structured packing or the random packings have horizontal surface portions.

9. The method as claimed in claim 8, wherein the structured packing is formed from structured sheet metal packings for vertical installation into the column having linear corrugations which subdivide the structured sheet metal packing into corrugated surfaces, wherein the angle of inclination of the corrugated surfaces to the horizontal is in the range from 90 to 45°.

10. The method as claimed in claim 6, wherein the structured packing or the random packings have a reduced resistance to flow at their surface.

11. The method as claimed in claim 7, wherein the structured packing is formed from rippled or corrugated layers, and between two rippled or corrugated layers in each case one flat intermediate layer is disposed, with the flat intermediate layers not extending to the edge of the structured packing or having, in the edge zone of the structured packing, an increased gas permeability.

12. The method as claimed in claim 7, wherein the structured packing is formed from structured sheet metal packings for vertical installation in to the column having a linear corrugations which subdivide the structured sheet metal packings into corrugated surfaces and which have a width a measured from corrugated edge to corrugated edge and perforations, wherein a proportion X of at least 60% of the perforations has a distance b of at most 0.4 a to the lower corrugated surface.

13. A process for preparing pseudoionone by aldolizing citral and acetone by reactive distillation in a column according to the definition in claim 6, which comprises operating the column with respect to its gas and liquid loading in such a manner that a maximum of from 50 to 95% of the flooding limit loading is reached.

14. A process for carrying out a heterogeneously catalyzed aldol condensation by reactive distillation in a column according to the definition in claim 6, which comprises the supported catalyst being regenerated by treatment with an aqueous alkaline solution, when the original catalyst activity decreases.

15. The method as claimed in claim 3, wherein the geometry of the catalyst support is determined in such a manner that the ratio of the external surface area to the volume is in the range from 1 to 5 $mm^{-1}$.

16. A method as claimed in claim 3, wherein the catalyst support is in the form of solid or hollow cylinders, spheres and honeycombs, trilobes or toothed wheels.

17. A method as claimed in claim 9, wherein the angle of inclination of the corrugated surfaces to the horizontal is 60°.

18. A method as claimed in claim 10, wherein the reduced resistance to flow at the surface of the structured packing or of the random packings is due to perforations and/or roughness of the material of the structured packing or of the random packings or by constructing the structured packing as expanded metal.

19. A method as claimed in claim 11, wherein the flat intermediate layers have holes in the edge zone of the structured packing.

* * * * *

UNITED STATES PATENT AND TRADEMARK OFFICE
CERTIFICATE OF CORRECTION

PATENT NO.         : 7,098,366 B2                                            Page 1 of 1
APPLICATION NO. : 10/497597
DATED              : August 29, 2006
INVENTOR(S)        : Sigl et al.

It is certified that error appears in the above-identified patent and that said Letters Patent is hereby corrected as shown below:

On the Title of the Patent, in item (22):
    "Dec. 2, 2002" should read --Dec. 5, 2002--

Signed and Sealed this

Tenth Day of April, 2007

JON W. DUDAS
*Director of the United States Patent and Trademark Office*